United States Patent [19]

Bantick et al.

[11] Patent Number: 5,428,044
[45] Date of Patent: Jun. 27, 1995

[54] ANTI-INFLAMMATORY 4-AMINOPHENYL DERIVATIVES

[75] Inventors: John R. Bantick; David N. Hardern; Richard A. Appleton, all of Leicestershire; John Dixon, Nr Melton Mowbray; David J. Wilkinson, Leicestershire, all of England

[73] Assignee: Fisons plc, Ipswich, England

[21] Appl. No.: 138,375

[22] Filed: Oct. 15, 1993

Related U.S. Application Data

[63] Continuation of Ser. No. 978,041, Nov. 18, 1992, abandoned, which is a continuation of Ser. No. 634,182, filed as PCT/GB90/00762, May 17, 1990, abandoned.

[30] Foreign Application Priority Data

| May 20, 1989 | [GB] | United Kingdom | 11654 |
| May 20, 1989 | [GB] | United Kingdom | 11655 |
| Feb. 10, 1990 | [GB] | United Kingdom | 3044 |

[51] Int. Cl.$^6$ ............... A61K 31/535; A01N 43/56; C07D 231/38; C07D 401/12
[52] U.S. Cl. ................... 514/341; 546/279; 514/407; 548/371.4; 548/371.7; 548/372.5; 548/364.1; 548/365.7
[58] Field of Search ............... 548/371.4, 371.7, 372.5, 548/364.1, 365.7; 514/487, 341; 546/279

[56] References Cited

U.S. PATENT DOCUMENTS

| 1,810,267 | 6/1931 | Desamari | 546/161 |
| 2,748,122 | 4/1956 | Burtner | 544/332 |
| 3,435,041 | 3/1969 | Drukker et al. | 546/161 |
| 3,853,895 | 12/1974 | Lamm et al. | 546/289 |
| 3,864,359 | 2/1975 | Marsico, Jr. et al. | 548/362 |
| 4,260,775 | 4/1981 | Plath et al. | 548/362 |
| 4,316,039 | 2/1982 | Plath et al | 548/362 |
| 4,383,851 | 5/1983 | Rogers et al. | 71/94 |
| 4,614,742 | 9/1986 | Ishikawa et al. | 514/237 |
| 4,803,216 | 2/1989 | Appleton et al. | 514/407 |
| 4,810,719 | 3/1989 | Appleton et al. | 514/406 |
| 4,868,183 | 9/1989 | Kanai et al. | 514/255 |
| 4,956,378 | 9/1990 | Burford et al. | 514/404 |

FOREIGN PATENT DOCUMENTS

| 0005559 | 11/1979 | European Pat. Off. |
| 0013143 | 7/1980 | European Pat. Off. |
| 0023766 | 2/1981 | European Pat. Off. |
| 0044266 | 1/1982 | European Pat. Off. |
| 0046138 | 2/1982 | European Pat. Off. |
| 0067630 | 12/1982 | European Pat. Off. |
| 0073931 | 3/1983 | European Pat. Off. |
| 0126254 | 11/1984 | European Pat. Off. |
| 0127371 | 12/1984 | European Pat. Off. |
| 0224339 | 6/1987 | European Pat. Off. |
| 0248523 | 12/1987 | European Pat. Off. |
| 0254259 | 1/1988 | European Pat. Off. |
| 0270138 | 6/1988 | European Pat. Off. |

OTHER PUBLICATIONS

Fuji Photo Film KK, Japanese Kokai (Abstract Only)5-2-42726, Apr. 1977.
Journal of Medicinal Chemistry, vol. 10, No. 3, May, 1967, pp. 427-431.

Primary Examiner—Mukund J. Shah
Assistant Examiner—Matthew V. Grumbling
Attorney, Agent, or Firm—Marshall, O'Toole, Gerstein, Murray & Borun

[57] ABSTRACT

There are disclosed compounds of the formula (I):

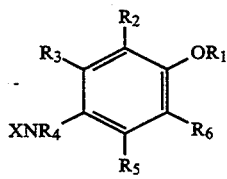

in which the variables $R_1$, $R_2$, $R_3$, $R_4$, $R_5$, $R_6$, and X are defined in the specification. The compounds are useful as pharmaceuticals, especially as anti-inflammatory agents.

4 Claims, No Drawings

ANTI-INFLAMMATORY 4-AMINOPHENYL DERIVATIVES

This is a continuation of U.S. application Ser. No. 07/978,041, filed Nov. 18, 1992; in turn a continuation of U.S. application Ser. No. 07/634,182, filed as PCT/GB90/00762, May 17, 1990, both now abandoned.

This invention relates to novel compounds, compositions thereof and methods for their preparation.

According to the invention there are provided compounds of formula I:

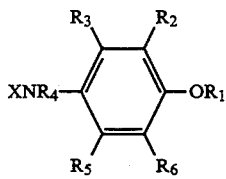

in which $R_1$ represents C(O)YZ or $SO_2R_{10}$,

Y represents a single bond, O, $NR_{11}$ or CO,

Z represents hydrogen, alkyl or alkyl substituted by one-or more substituents selected from hydroxy, alkoxy, acyloxy, carboxy, alkoxycarbonyl, $CONR_{12}R_{13}$, arylalkoxy, $Ar_1$, heterocycle, halo, cyano or $NR_{14}R_{15}$, $R_2$, $R_3$, $R_5$ and $R_6$, which may be the same or different, represent hydrogen, alkyl, alkoxy or halogen, $R_4$ and $R_{11}$, which may be the same or different, represent hydrogen or alkyl, $R_{10}$ represents alkyl, X represents a heterocycle optionally substituted by one or more substituents selected from alkyl, cycloalkyl, alkoxy, alkoxycarbonyl, carboxy, hydroxyalkyl, halo, $CONR_{16}R_{17}$, $NR_{18}R_{19}$, or $Ar_2$, $Ar_1$ and $Ar_2$ which may be the same or different represent aryl or aryl substituted by one or more substituents selected from halogen, nitro, alkoxy, carboxy, alkyl or trihaloalkyl, $R_{12}$, $R_{13}$, $R_{14}$, $R_{15}$, $R_{16}$, $R_{17}$, $R_{18}$ and $R_{19}$, which may be the same or different, represent hydrogen, alkyl or benzyloxycarbonyl, or a pharmaceutically acceptable N-oxide, N-alkyl, salt, ester or amide derivative thereof, for use as a pharmaceutical.

According to the invention there are also provided the novel compounds of formula I and derivatives thereof, as defined above, provided that at least one of $R_2$ and $R_6$ is other that hydrogen.

According to the invention there is further provided a process for the preparation of compounds of formula I which comprises a) reacting a compound of formula II, $$X\text{—}L_1 \qquad \text{II}$$

in which $L_1$ is a leaving group and X is as defined in claim 1, with a compound of formula III,

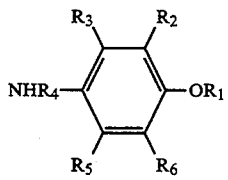

in which $R_1$, $R_2$, $R_3$, $R_4$, $R_5$ and $R_6$ are as defined in claim 1, b) reacting a compound of formula IV,

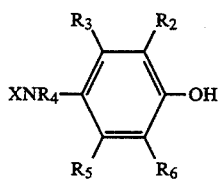

in which X, $R_2$, $R_3$, $R_4$, $R_5$ and $R_6$ are as defined above, with a compound of formula V, $$R_1L_2 \qquad \text{V}$$

in which $L_2$ is a leaving group and $R_1$ is as defined above, c) producing a compound of formula I in which X represents an unsaturated heterocycle, by oxidising a corresponding compound of formula VI,

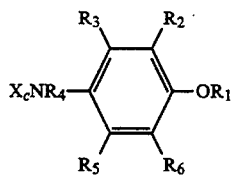

in which Xc represents a corresponding heterocycle more saturated than X, and $R_1$, $R_2$, $R_3$, $R_4$, $R_5$ and $R_6$ are as defined above, d) producing a compound of formula I which bears one or more alkyl substituents containing at least two carbon atoms, by reducing a corresponding compound of formula I, in which the appropriate substituent(s) contains one or more double or treble carbon-carbon bonds, e) producing a compound of formula I, in which X is substituted by cyclohexyl, by reducing a corresponding compound of formula I in which X is substituted by phenyl.

f) producing a compound of formula I substituted by one or more of OH, $NHR_{14}$ or COOH, which comprises removing a protecting group from a corresponding compound of formula I bearing a protected OH, $NHR_{14}$ or COOH group.

g) producing a compound of formula I, in which Z represents alkyl substituted by cyano, by reacting a corresponding compound of formula I in which Z represents alkyl substituted by halogen, with a cyanide salt, h) producing a compound of formula I, which is a N-alkyl salt, by reacting a corresponding compound of formula I in which X represents a nitrogen containing heterocycle, with an alkylating agent, and where desired or necessary converting the resulting compound of formula I into a pharmaceutically acceptable N-oxide, N-acetyl, salt, ester or amide thereof, or vice versa.

In process (a), leaving groups that $L_1$ may represent include, for example, halogen, eg chlorine or bromine; arylsulfonyl; hydroxy and esters thereof; alkoxy, eg methoxy or ethoxy; dihalophosphonyl, eg dichloro- or dibromo-phosphonyl; and $-NR_aR_b$, where $R_a$ and $R_b$ may each independently represent hydrogen or alkyl C1 to C6.

The reaction may be carried out with or without a solvent. When the reaction is carried out using a solvent, the solvent is preferably inert to the conditions of the reaction, and may be for example, a polar solvent such as 1,4-dioxan, ethanol, acetic acid, acetonitrile or dimethylformamide. However apolar solvents, eg toluene, may also be used. The reaction is preferably carried out at a temperature of from about 25° to 200° C.

In process (b), leaving groups that $L_2$ may represent include Oacyl (ie compound V is an acid anhydride), tosylate, mesylate, imidazolide, bromide or, preferably, chloride. The reaction may be carried out by mixing the reagents in anhydrous conditions in the presence of an inert solvent such as dichloromethane. When the reagent of formula V is an acid halide, the reaction is preferably carried out in the presence of a base such as triethylamine and/or dimethylaminopyridine.

In certain cases, for example when both $R_2$ and $R_6$ represent bulky groups such as tertiary butyl, Schotten Baumann conditions, in which the reaction is carried out using a base strong enough to abstract a proton from the phenol of formula IV, give particularly good results. A particularly suitable base that may be mentioned is potassium tert-butoxide.

Oxidising agents that may be used in process (c) for the oxidation of heterocycles Xc include metal catalysts, organic and inorganic oxidising agents, hypohalites and peroxides. Preferred metal catalysts include palladium on charcoal in the presence or absence of air. Preferred inorganic oxidising agents include manganese dioxide and chromium trioxide. Suitable organic oxidising agents include peracids, eg 3-chloroperbenzoic acid, and easily reduced hydrogen acceptors, eg 2,3-dichloro-5,6-dicyano-1,4-benzoquinone (DDQ) and organic hypohalites such as tertiary butyl hypochlorite. The oxidation may be carried out in a solvent which is inert to the reaction conditions. The choice of solvent depends on the compound to be oxidized and on the oxidizing agent. However, suitable solvents include halogenated hydrocarbons such as dichloromethane, alcohols, eg ethanol and aromatic hydrocarbons, eg toluene. The reaction may be carried out at a temperature of about 0° to 150° C.

The reduction of process (d) may be carried out using hydrogen and an appropriate metal catalyst, for example 10% palladium or rhodium on an inert support, such as charcoal. The reaction may be carried out in an inert solvent, for example ethanol, at a pressure of from 1 to 10 atmospheres of hydrogen.

The reduction of process (e) may be carried out under conditions generally similar to those described above for process (d).

Removal of the protecting groups in process (f) depends on the nature of the protecting groups, but in general conventional techniques may be employed, including acidic, basic, electrolytic, photolytic and particularly hydrogenolytic methods. Protecting groups which may be mentioned include benzyl (Bzl); benzyloxycarbonyl (CBz) or butyloxycarbonyl (Boc). Benzyl protecting groups Bzl and CBz may be removed by hydrogenolysis, for example by reaction with hydrogen in a suitable solvent such as an alcohol in the presence of a transition metal catalyst such as palladium on carbon. The Boc protecting group may be removed by treatment with acid, eg trifluoroacetic acid.

In process (g), the displacement of the halogen may be carried out in a solvent which is inert to the reaction conditions. We particularly prefer a polar aprotic solvent, for example acetonitrile, dimethyl formamide or dimethyl sulfoxide. The reaction may be carried out at a temperature of from about 0° to 100° C.

The alkylation of process (h) may be carried out using an excess of the alkylating agent as solvent or using a solvent which is inert to the reaction conditions. We particularly prefer a polar aprotic solvent, for example acetonitrile, dimethyl formamide or dimethyl sulfoxide. The reaction may be carried out at a temperature of from about 0° to 100° C. Suitable alkylating agents include alkyl halides, for example, methyl iodide, and alkyl tosylates.

Compounds of formula II may be prepared from the corresponding 4-aminophenol, by the method of process b). Such 4-aminophenols are either known or may be made from known compounds using conventional methods.

Certain compounds of formula IV are known from either EP-A-254 259 or EP-A-178 035. Certain intermediates of formula IV are novel. Thus according to a further aspect of the invention there are provided compounds of formula IVa,

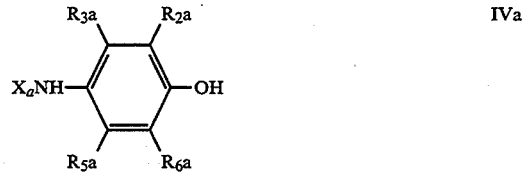

in which $X_a$ represents 1H-pyrazol-3-yl substituted by 1-phenyl or 1-trifluromethylphenyl, $R_{2a}$ and $R_{6a}$, which may be the same or different, are selected from lower alkyl, halogen and lower alkoxy, and both $R_{3a}$ and $R_{5a}$ represent hydrogen.

The novel phenols of formula IVa may be made by the methods indicated in the European applications Cited above or by the methods described herein.

Compounds of formula VI may be prepared by methods analogous to those described in processes (a), (b), (d), (e), (f), (g) or (h).

The compounds of formulae II and V are either known or may be made from known compounds by conventional techniques known per se.

The acid addition salts of compounds of formula I may be prepared by reaction of the free base with an appropriate acid. The acid addition salts may be converted to the corresponding free base by the action of a stronger base.

The processes as described above may produce compounds of formula I or derivatives thereof. It is also within the scope of this invention to treat any derivative so produced to liberate the free compound of formula I, or to convert one derivative into another.

Pharmaceutically acceptable derivatives of compounds of formula I include pharmaceutically acceptable acid addition salts. Suitable salts include salts of mineral acids, for example, hydrohalic acids, e.g. hydrochloric acid or hydrobromic acid, or organic acids, e.g. formic, acetic or lactic acids. The acid may be polybasic, for example sulfuric, fumaric or citric acid.

When the compound of formula I contains a carboxylic acid group, it may form pharmaceutically acceptable salt, ester and amide derivatives. Suitable salts include ammonium, alkali metal (eg sodium, potassium and lithium) and alkaline earth metal (eg calcium or magnesium) salts, and salts with suitable organic bases, eg salts with hydroxylamine, lower alkylamines such as methylamine or ethylamine, with substituted lower alkylamines, eg hydroxy substituted alkylamines such as tris(hydroxymethyl)methylamine or triethanolamine, with simple monocyclic nitrogen heterocyclic compounds, eg pyridine or morpholine, with an amino acid, eg lysine, ornithine, arginine, or an N-alkyl, especially an N-methyl derivative of any one thereof, or with an aminosugar, eg glucamine, N-methyl-glucamine or glucosamine. Suitable esters include simple lower alkyl esters, eg ethyl ester. esters derived from alcohols containing basic groups, eg bis-lower alkylamino substituted alkanols such as the 2-(diethylamino)ethyl ester, and acyloxy alkyl esters, eg a lower acyloxy-lower alkyl ester such as the pivaloyloxymethyl ester. The pharmaceutically acceptable acid addition salts of the basic esters, eg the hydrochloride, the hydrobromide, the maleate or the fumarate salts, may also be used. The esters may be made by conventional techniques, eg esterification or transesterification. The amides may be, for example, unsubstituted or mono- or di- C1 to 6 alkyl or phenyl amides and may be made by conventional techniques, eg reaction of an ester of the corresponding acid with ammonia or an appropriate amine.

We prefer compounds of formula I in which $R_1$ represents C(O)YZ.

Particular values of $Ar_1$ that Z may represent include optionally substituted mono- and bicyclic aromatic species, for example naphthalene, and particularly, phenyl.

We prefer compounds in which $Ar_1$ is either unsubstituted or bears one substituent selected from halogen, eg chlorine, nitro, lower alkoxy, especially methoxy or carboxy.

When Z represents a heterocycle, the heterocycle may be unsubstituted or substituted by one or more substituents selected from alkyl, cycloalkyl, alkoxy, alkoxycarbonyl, carboxy, hydroxyalkyl, halo, $CONH_2$, $NH_2$ or phenyl. We prefer the heterocycle to be a 5- or 6-membered heterocyclic ring containing 1 to 3 heteroatoms selected from nitrogen, oxygen and sulfur. Particular heterocycles that may be mentioned include furan, pyrrole, pyrazole, thiophene and especially pyridine. Suitable heterocyclic derivatives that Z may represent include pyridine N-oxide and N-alkyl pyridine, eg N-methyl pyridine.

When Y is O, we prefer Z to represent alkyl, especially lower alkyl, for example methyl, ethyl or butyl; or phenyl.

When Y is $NR_{11}$, we prefer Z to represent hydrogen or lower alkyl.

When Y is CO, we prefer Z to represent alkyl, eg lower alkyl such as methyl, ethyl or butyl.

However, we prefer compounds in which Y is a single bond. When Y is a single bond we prefer Z to be other than hydrogen. When Z represents alkyl, we prefer alkyl to represent lower alkyl, especially alkyl C1 to C4. The alkyl group may be saturated or unsaturated and straight or branched. Particular alkyl groups that may be mentioned include methyl, ethyl, n-propyl, iso propyl, n-butyl and tertbutyl. When the alkyl is substituted we prefer it to be tri-, di- and especially mono-substituted. The substituent(s) may be located on any part of the alkyl group. However we prefer those compounds which contain a single substituent located at the terminus of the alkyl group, specific substituents that may be mentioned include hydroxy; lower alkoxy, eg methoxy or ethoxy; lower acyloxy, particularly $C_1$ to $C_4$ acyloxy, for example acetoxy, propanoyloxy; $CONH_2$; phenlyalkoxy, particularly phenylmethoxy; halogen, particularly bromine and especially chlorine; cyano or $NH_2$.

Particularly preferred groups that $R_1$ may represent include acetyl and acetyl subsituted by cyano or lower alkoxy.

We prefer compounds of formula I in which at least one of $R_2$, $R_3$, $R_5$ and $R_6$ is other than hydrogen. We particularly prefer those compounds in which at least two of $R_2$, $R_3$, $R_5$ and $R_6$ is other than hydrogen. Especially preferred are those compounds in which $R_2$ and $R_6$ are other than hydrogen. We prefer compounds in which at least one of $R_2$ and $R_6$ is alkyl. When one or more of $R_2$, $R_3$, $R_4$, $R_5$ or $R_6$ is alkyl, it may be saturated or unsaturated and straight or branched. We particularly prefer those compounds in which both $R_2$ and $R_6$ are alkyl, preferably lower alkyl, for example selected from methyl, ethyl, propyl, propenyl and butyl. Compounds in which $R_2$ and $R_6$ are the same are especially preferred. We also prefer compounds in which at least one, and preferably both, of $R_3$ and $R_5$ are hydrogen.

We prefer compounds in which $R_4$ is lower alkyl, eg methyl, ethyl or propyl, and especially hydrogen We prefer compounds in which $R_{10}$ is lower alkyl, and especially methyl, ethyl or propyl.

Substituents that $R_{11}$ may particularly represent include hydrogen and lower alkyl, for example, methyl, ethyl or propyl.

Heterocycles that X may particularly represent may be unsubstituted or substituted by one, two or three substituents. The heterocycle may be saturated, partially saturated or fully unsaturated.

Heterocycles that may be particularly mentioned include those having a single or fused ring system, comprising from, for example, 2-4 rings and containing from one to five heteroatoms. Heteroatoms that may be particularly mentioned include nitrogen, oxygen and sulfur.

We prefer heterocycles having from 5 to 10 ring atoms. In particular, we prefer X to represent a 5- or 6-membered heterocyclic ring containing 1 to 3 heteroatoms selected from nitrogen, oxygen and sulfur.

Particular heterocyclic groups that X may represent include pyrroyl, furyl, thienyl, pyrazolyl, imidazolyl, benzimidazolyl, oxazolyl, isoxazolyl, triazolyl, thiadiazolyl, oxadiazolyl, triazinyl, pyrazinyl, pyridinyl, quinolinyl, pyrimidinyl, pyridazinyl and tetrahydronaphthopyranyl.

Typical groups that X may represent include 1-pyrroyl, 2-furyl, 3-furyl, 2-thienyl, 3-thienyl, 1H-3-pyrazolyl, 2-imidazolyl, 2-benzimidazolyl, 2-oxazolyl, 4-oxazolyl, 3-isoxazolyl, 4-isoxazolyl, 5-isoxazolyl, 1,2,3-triazoly-1-1, 1,2,3-triazoly-4-1, 1,2,4-thiadiazol-3-yl, 1,2,3-oxadiazol-5-yl, 1,2,4-oxadiazol-5-yl, 1,2,4-triazin-3-yl, 1,2,4-triazin-5-yl, 1,2,4-triazin-6-yl, pyrazinyl, pyridin-2-yl, pyridin-4-yl, quinolin-2-yl, quinolin-4-yl, 2-pyrimidinyl, 4-pyrimidinyl, 3-pyridazinyl and 6,7,8,9-tetrahydronaphtho[2,3b]pyran-2-yl.

When X is substituted, we particularly prefer it to be substituted by three, two or most preferably, one substituent selected from alkyl, particularly lower alkyl, especially methyl, ethyl, propyl or butyl; cycloalkyl, eg cyclobutyl, cyclopentyl, cycloheptyl and particularly cyclohexyl; alkoxy, particularly lower alkoxy, especially alkoxy C1 to C4; alkoxycarbonyl, particularly lower alkoxycarbonyl, especially methoxycarbonyl, ethoxycarbonyl, propoxycarbonyl, isopropoxycarbonyl, butoxycarbonyl and tert butoxycarbonyl; carboxy; hydroxyalkyl, particularly hydroxy lower alkyl including monohydroxy, C1–C6 alkyl groups such as hydroxymethyl, 2-hydroxyethyl, 3-hydroxypropyl; halogen, including chlorine, fluorine, bromine and iodine; amino or $Ar_2$. Particular aryl groups that $Ar_2$ may represent include naphthalenyl and particularly phenyl, optionally substituted by three, two or, preferably, one substituent selected from halogen, eg chloro, fluoro or bromo; alkoxy, preferably lower alkoxy, eg methoxy or ethoxy; carboxy; alkyl, particularly lower alkyl, for example methyl, ethyl, propyl or trihaloalkyl, particularly trihaloloweralkyl, especially $CF_3$ or $CH_2CF_3$.

We particularly prefer those compounds in which X represents 1H-pyrazol-3-yl optionally substituted by phenyl, especially 1-phenyl.

Compounds of formula I, and pharmaceutically acceptable derivatives thereof, are useful because they possess pharmacological activity in animals. In particular, the compounds are useful as broad spectrum anti-inflammatory agents as indicated in one or more of the following assay systems:

(a) Inhibition of lipoxygenases, e.g. 5, 12 and 15 lipoxygenase, in the presence of exogenous arachidonic acid and measurement of the enzyme activity by either a modification of B. A. Jakschik et al, Biochemical and Biophysical Research Communications, 95(1), 103, (1980) using reverse phase HPLC to quantify the products or by a modification of the method of F. F. Sun et al, Prostaglandins 21 (2) 333 (1981) using uv absorption to quantify product formation.

(b) Inhibition of prostaglandin synthetase, utilising movine seminal vesicle microsomes as the enzyme source after the method of Egan et al Biochemistry 17, 2230 (1978) using either radiolabelled arachidonic acid as substrate and product separation by thin layer chromatography and quantification by scintillation counting or unlabelled arachidonic acid as substrate and a specific radioimmunoassay kit (New England Nuclear) to measure prostaglandin E2 produced.

(c) Inhibition of 5 lipoxygenase activity in intact human neutrophils stimulated by ionophore A23187 and supplemented with exogenous arachidonic acid after the method of P Borgeat and B Samuelsson, Proceedings New York Academy of Science 70 2148 (1979) using reverse phase HPLC to measure the products.

(d) Inhibition of formation of arachidonic acid metabolites by mouse peritoneal macrophages challenged in vitro with immune complexes by the method of Blackham et al, J. Pharm. Pharmac. 37, 787, (1985).

(e) Inhibition of PGE2 formation and cell infiltration in the carrageenin sponge model by the method of Higgs et al, Eur. J. Pharmac. 66 81 (1980).

(f) Inhibition of immune complex mediated inflammation in the mouse peritoneal cavity by the method of Blackham et al, J. Pharmac. Methods 15, 77, (1985).

(g) Inhibition of carrageenin oedema in the rat by the method of Winter et al, Proc. Soc. Exp. Biol. 111 544 (1962).

(h) Inhibition of bronchial anaphylaxis in guinea pigs by the method of Anderson, Br. J. Pharmac. 77 301 (1982).

(i) Inhibition of oedema and eicosanoid production in mouse ears treated with arachidonic acid after the methods of Young et al, J. Invest. Derm. 82, 367, (1984) and Opas et al, J. Invest. Derm. 84,253, (1985).

The compounds are indicated for use in the treatment or prophylaxis of inflammatory conditions in mammals, including man. Conditions that may be specifically mentioned are: rheumatoid arthritis, rheumatoid spondylitis, osteoarthritis, gouty arthritis, and other arthritic conditions, inflamed joints;

eczema, psoriasis, burns, including sunburn, ulcers, wounds, acne or other inflammatory skin conditions such as sunburn;

inflammatory eye conditions including conjunctivitis and uveitis; lung disorders in which inflammation is involved, eg asthma, bronchitis, pigeon fancier's disease and farmer's lung;

conditions of the ear including otitis externa;

conditions of the gastrointestinal tract including aphthous ulcers, gingivitis, Crohn's disease (a condition of the small, and sometimes also of the large intestine), atrophic gastritis and gastritis varialoforme (conditions of the stomach), ulcerative colitis (a condition of the large intestine and sometimes the small intestine) coeliac disease (a condition of the small intestine), regional ileitis (a regional inflammatory condition of the terminal ileum), peptic ulceration (a condition of the stomach and duodenum) and irritable bowel syndrome; pyresis, pain;

and other conditions associated with inflammation, particularly those in which lipoxygenase and cyclooxygenase products are a factor.

The compounds of the invention may be used on their own or in combination with other drugs, for example:

for the treatment, in particular, of colitis, Crohn's disease and psoriasis: steroids, particularly those steroids which are eliminated presystemically, salazopyrin, keratolytic agents such as salicylic acid or purified coal tar fractions, dithranol, vitamins, for example vitamins A, D or E, antifungal agents such as benzuldazic acid, hexetidine, enilconazole or other azole antifungals, natamycin, polynoxylin, providone-iodine, griseofulvin and 2,4,6-tribromotoluene;

for the treatment of eczema the compounds may be combined with steroids or with antipruritic agents such as crotamition;

for the treatment of acne the compounds may be combined with bezoyl peroxide or tretonin;

for the treatment of seborrheic dermatitis the compounds may be combined with selenium sulphide, coal tar fractions, zinc pyrithione, sulfur, salicylic acid or steroids;

for the treatment of rosacea the compounds may combined with sulfur, particularly in the form of an ointment.

For the above mentioned uses the dosage administered will, of course, vary with the compound employed, the mode of administration and the treatment desired. However, in general satisfactory results are obtained when the compound is administered at a daily dosage of from about 0.1 mg to about 60 mg per kg of animal body weight, preferably given in divided doses 1 to 4 times a day or in sustained release form. For man the total daily dose is in the range of from 7.0 mg to 4.2 g and unit dosage forms suitable for oral administration comprise from 2.0 mg to 4.2 g of the compound admixed with a solid or liquid pharmaceutical carrier or diluent.

Compounds of formula I, and pharmaceutically acceptable derivatives thereof, may be used on their own or in the form of appropriate medicinal preparations for enteral including topical, or parenteral administration. Thus the new compound may be compounded with inorganic or organic, pharmaceutically acceptable adjuvants, diluents or carriers. Examples of such adjuvants, diluents and carriers are: for tablets and dragees: lactose, starch, talc, stearic acid; for capsules: tartaric acid or lactose; for injectable solutions: water, alcohols, glycerin, vegetable oils; for suppositories: natural or hardened oils or waxes.

Compositions in a form suitable for oral, ie aqueous or non aqueous suspensions or semi-solid gels, oesophageal administration include pills, capsules and tablets; particular tablets that may be mentioned include enteric coated, dispensible, effervescent, chewable and formulations intended for sublingual and buccal absorbtion.

Compositions in a form suitable for administration to the lung include formulations in inhalers, atomizers, nebulizers or insufflators as aerosols, particularly pressurised aerosols;

Compositions for rectal administration include suppositories or enemas, composition for parenteral delivery by injection (intravenous, subcutaneous, intramuseable) include cosolvent solutions, suspensions, emulsions, oils for parenteral delivery;

Compositions in a form suitable for topical administration to the skin include ointments, creams, oil-in-water emulsions or water-in-oil emulsion; aqueous or organic gels (for example celluloses or carboxyvinylpolymers).

compositions in a form suitable for topical administration to the eye or nose include solutions, suspensions, semi-solid gels, ointments and emulsions.

We prefer the composition to contain up to 50% and more preferably up to 25% by weight of the compound of formula I, or of the pharmaceutically acceptable derivative thereof.

The compound of formula I and pharmaceutically acceptable derivatives thereof have the advantage that they are less toxic, more efficacious, are longer acting, have a broader range of activity, are more potent, produce fewer side effects, more selective, are more easily absorbed, more stable or have other useful pharmacological properties, than compounds of similar structure.

The invention is illustrated by the following examples, in which temperatures are given in degrees celsius.

A. PREPARATION OF INTERMEDIATES

Example A 4-amino-2,6-dimethylphenyl acetate

To 2,6-dimethyl-4-nitrophenol (10 g) and triethylamine (21 ml) in dry dichloromethane (100 ml) at 0° was added acetyl chloride (5.6 ml) slowly. After 16 hours the mixture was washed with water, dried and evaporated to give the acetate (9.4 g), mp 109°–110°. The acetate (9.4 g) was hydrogenated in ethanol at atmospheric pressure over platinum oxide for 4 hours. Filtration, evaporation, and crystallisation (ethyl acetate/hexane) of the residue gave the title acetate (5.6 g), mp 82°–83°.

Example B 4-amino-3,6-dimethoxy-2-methylphenol

Sulfanilic acid (10.8 g) was diazotised as in "Organic Syntheses" Coll. Vol. 2, p 35. After 20 minutes the resulting suspension was added to an ice-cold solution of 3,6-dimethoxy-2-methylphenol (8.1 g) and sodium hydroxide (10.8 g) in water (100 ml). After one hour the mixture was heated to 45°–50° and sodium hydrosulfite (22.2 g) was added in portions. When the red dye colour was discharged the mixture was cooled to give a yellow precipitate of the bisulfite salt (10 g) of the title phenol.

Example C

Using the method of Example B above, the following phenols were prepared via their bisulfite salts:
a) 4-amino-2,6-dimethylphenol;
b) 4-amino-2,3,4,5-tetramethylphenol;
c) 4-amino-2,6-bis(1,1-dimethylethyl)phenol.

Example D 2,6-dimethyl-4-(1-phenyl-1H-pyrazol-3-yl)aminophenol 2,6-dimethyl-4-aminophenol (15 g) and 4,5-dihydro-1-phenyl-1H-pyrazol-3-amine (17.6 g) were heated with p-toluene sulfonic acid (0.2 g) at 160° for 1 hour under nitrogen. The mix was cooled, taken up in dichloromethane and washed with dilute HCl, and water. Evaporation, and chromatography of the residue (silica, dichloromethane/ethyl acetate [9:1]) gave 4-(4,5-dihydro-1-phenyl-1H-pyrazol-3-yl)amino-2,6-dimethylphenol (14.2 g), mp 154°–158°. This was refluxed in toluene (40 ml) with 10% palladium on charcoal (10 g) for 3 hours. The mixture was filtered and evaporated to give, after crystallisation from cyclohexane/ethyl acetate, the title compound (8 g), mp 154°–155°.

Example E

The following intermediates were made by the method of Example D:
a) 2,3,5,6-tetramethyl-4-(1-phenyl-1H-pyrazol-3-yl)amino phenol, mp 160°–162°;
b) 3,6-dimethoxy-2-methyl-4-(1-phenyl-1H-pyrazol-3-yl) aminophenol, mp 107°–108°;
c) 2,6-bis(1,1-dimethylethyl)-3-(1-phenyl-1H-pyrazol-3-yl) aminophenol, mp 114°–115°;
d) 2,6-dichloro-4-(1-phenyl-1H-pyrazol-3-yl)aminophenol, mp 144°–146°.

Example F 2,6-dimethyl-4-[N-methyl-N-(1-phenyl-1H-pyrazol-3-yl) amino]phenol To 2,6-dimethyl-4-(1-phenyl-1H-pyrazol-3-yl)amino phenol (8 g), acetic acid (2.8 ml), and aqueous 40% formaldehyde (3.1 ml) in acetonitrile (40 ml) was added sodium cyanoborohydride (5.4 g). After 2 hours the mixure was quenched with water and extracted with dichloromethane. The organic phase was washed with aqueous sodium bicarbonate solution, then water, dried, evaporated and chromatographed (silica, dichloromethane) to give the title product (3 g), mp 139°–140° (from ethanol).

Example G

The following intermediates was prepared by the method of Example F:
a) 2,6-bis(1,1-dimethylethyl)-4-[N-methyl-N-(1-phenyl-1H-pyrazol-3-yl)amino]phenol, mp 117°–118°.

Example H

2-Ethylsulfinyl-6,7,8,9-tetrahydro-4H-1-naphtho [2,3-b]pyran-4-one

The title compound (mp 158°–159°) was prepared from 1-(3-hydroxy-6,7,8,9-tetrahydronaphthalene-2-yl)ethanone by condensation with carbon disulfide, alkylation with ethyl iodide, and oxidation according to the methods in J. Heterocyclic Chem., 1981, 18, 679.

Example I

5,6-Diethoxy-2-methylsulfonyl-1H-benzimidazole

The title compound (mp 182°–184°) was prepared from 5,6-diethoxy-1,3-dihydro-2H-benzimidazole-2-thione by alkylation (methyl iodide) and oxidation.

Example J

The following were prepared from the appropriate amino heterocycle by the methods described in EP-A-254 259:

a) 2,6-dimethyl-4-(pyrazin-2-yl)aminophenol, mp 188°–190°;

b) 4-(4-chloro-6-methylpyrimidin-2-yl)amino-2,6-dimethyl phenol, mp 160°–163°.

B. PREPARATION OF COMPOUNDS OF FORMULA I

The following compounds of formula I were prepared from the intermediates described above or from compounds known in the art, including those described in EP-A-254 259 and EP-A-178 035.

Example 1

4-[4,5-Dihydro-1-phenyl-1H-pyrazol-3-yl]amino-2,6-di methylphenyl acetate 4,5-Dihydro-1-phenyl-1H-pyrazol-3-amine (0.16 g), 4-amino-2,6-dimethylphenyl acetate (0.2 g), and toluene-4-sulfonic acid (0.02 g) were refluxed in toluene under nitrogen for 8 hours. Evaporation and chromatography (silica, dichloromethane/ethyl acetate [95:5]) of the residue gave the title product (0.15 g), as a solid.

Example 2

Using the method of Example 1, the following compound were prepared:

a) 4-[4,5-Dihydro-1-(3-trifluoromethylphenyl)-1H-pyrazol-3-yl]amino-2,6-dimethylphenyl acetate, mp 190°–191°.

b) 2,6-Dimethyl-4-[6,7,8,9-tetrahydro-4-oxo-4H-1-naphtho [2,3-b]pyran-2-yl]aminophenyl acetate, (from the intermediate sulfoxide of Example H), mp 224°–226° c) 4-(5,6-Diethoxy-1H-benzimidazol-2-yl)amino-2,6-dimethylphenyl acetate, (from the intermediate of Example I), mp 91°–94° d) 2,6-dimethyl-4-(quinolin-2-yl)aminophenyl acetate, (from 2-chloroquinoline), mp 154–155;

e) 4-(3-aminocarbonylpyridin-2-yl)amino-2,6-dimethylphenyl acetate, (from 2-chloronicotinamide), mp 209–211;

f) 2,6-dimethyl-4-(2-pyrimidinyl)aminophenyl acetate, (from 2-chloropyrimidine).

Example 3

4-(1-Phenyl-1H-pyrazol-3-yl)amino-2,6-di(prop-2-enyl) phenyl acetate (a) 4-(1-Phenyl-1H-pyrazol-3-yl)amino-2-(prop-2-enyl) phenol 4-(1-Phenyl-1H-pyrazol-3-yl)aminophenyl (19 g) was added to sodium hydride (4.0 g of a 50% suspension, freed from oil) in dry dimethyl formamide (150 ml). After 0.5 hr, allyl bromide (7.2 ml) was added, and the mixture was stirred for 16 hours, poured into water, and extracted with ethyl acetate. Evaporation of solvent and chromatography (silica/dichloromethane) gave 1-phenyl-N-(4-[prop-2-enyl]oxyphenyl)-1H-pyrazol-3-amine (21.9 g), mp 80°–81°. This solid (2.9 g) was heated at 200° under nitrogen for 5 hours. Chromatography (silica/dichloromethane) gave the sub-title product as a viscous oil (1.4 g). Salient $^1$HNMR (DMSO): δ8.7 (1H, s, NH); 8.4 (1H, s, OH); 6.0 (1H, m, —CH=); 5.1 (2H, dd, =CH$_2$); 3.25 (2H, d, OCH$_2$).

(b) 4- (1-Phenyl-1H-pyrazol-3-yl)amino-2,6-di(prop-2-enyl)phenol

The sub-title product from (a) (10.5 g) was converted by analogous processes to (a) to 1-phenyl-N-(3-[prop-2-enyl]-4-[prop-2-enyl]oxyphenyl)-1H-pyrazol-3-amine (7.6 g, oil) and then to the sub-title phenol (5.5 g), mp 87°–88°.

(c) 4-(1-Phenyl-1H-pyrazol-3-yl)amino-2,6-di(prop-2-enyl)phenyl acetate

To the product from step (b) (5.0 g) in dichloromethane (100 ml) containing 4-dimethylaminopyridine (10 mg) and triethylamine (2.1 ml) was added acetyl chloride (1.1 ml) slowly with stirring. After 6 hours water was added, and the residue after evaporation of the organic phase was chromatographed (silica/dichloromethane), and then crystallised from cyclohexane to afford the title product (4.5 g), mp 110°–111°.

Example 4

The following compounds were made by the method of Example 3c), from the corresponding phenol and appropriate carbonyl or sulfonyl chloride:

a) 2,6-dimethyl-4-(1-phenyl-1H-pyrazol-3-yl)aminophenyl butanoate, mp 138°–140°;

b) 2,6-dimethyl-4-(1-phenyl-1H-pyrazol-3-yl)aminophenyl 2,2-dimethylpropanoate, mp 139°–140°;

c) 2,6-dimethyl-4-(1-phenyl-1H-pyrazol-3-yl)aminophenyl phenyl carbonate, mp 138°–139°;

d) 2,6-dimethyl-4-(1-phenyl-1H-pyrazol-3-yl)aminophenyl methyl carbonate, mp 110°–112°;

e) 2,6-dimethyl-4-(1-phenyl-1H-pyrazol-3-yl)aminophenyl benzoate, mp 117°–118°;

f) 2,6-dimethyl-4-(1-phenyl-1H-pyrazol-3-yl)aminophenyl methanesulfonate, mp 144°–145°;

g) 2,6-dimethyl-4-(1-phenyl-1H-pyrazol-3-yl)aminophenyl 2-methylpropanoate, mp 127°–128°;

h) 2,6-dimethyl-4-(1-phenyl-1H-pyrazol-3-yl)aminophenyl phenylmethyl carbonate, mp 105°–106°;

i) 2,6-dimethyl-4-(1-phenyl-1H-pyrazol-3-yl)aminophenyl 4-methoxybenzoate, mp 185°–187°;

j) 2,6-dimethyl-4-(1-phenyl-1H-pyrazol-3-yl)aminophenyl methoxyacetate, mp 149°–150°;

k) 2,6-dimethyl-4-(1-phenyl-1H-pyrazol-3-yl)aminophenyl chloroacetate, mp 141°–142°;

l) 2,6-dimethyl-4-(1-phenyl-1H-pyrazol-3-yl)aminophenyl (1,1-dimethylethyl)carbonate, mp 122°–123°;

m) 2,6-dimethyl-4-(1-phenyl-1H-pyrazol-3-yl)aminophenyl 4-nitrobenzoate, mp 210°–211°;

n) 2,6-dimethyl-4-(1-phenyl-1H-pyrazol-3-yl)aminophenyl butyl carbonate, mp 72°–73°;

o) 2,6-dimethyl-4-(1-phenyl-1H-pyrazol-3-yl)aminophenyl 3-pyridinecarboxylate, mp 158°–160°;

p) 4-(4-Chloro-6-methylpyrimidin-2-yl)amino-2,6-dimethylphenyl acetate, mp 143°–144°;

q) 4-(4-Chloro-6-methylpyrimidin-2-yl)amino-2,6-dimethylphenyl methoxyacetate, mp 126°–127°;

r) 2,6-dimethyl-4-(pyrazin-2-yl)aminophenyl acetate, mp 176°–177°;

s) 2,6-dimethyl-4-(1-phenyl-1H-pyrazol-3-yl)aminophenyl 4-chlorobenzoate, mp 166°–167°;

t) 2,6-dimethyl-4-(1-phenyl-1H-pyrazol-3-yl)aminophenyl 3-methoxypropanoate, mp125°–126°;

u) 2,6-dimethyl-4-(1-phenyl-1H-pyrazol-3-yl)aminophenyl dimethylcarbamate, mp 171°–173°;

v) 2,6-dimethyl-4-(1-phenyl-1H-pyrazol-3-yl)aminophenyl 4-dimethylamino-4-oxobutanoate, mp 210°–211°;

w) 2,6-dimethyl-4-(1-phenyl-1H-pyrazol-3-yl)aminophenyl acetoxyethanoate, mp 127°–128°;

x) methyl 2,6-dimethyl-4-(1-phenyl-1H-pyrazol-3-yl)aminophenyl propanedioate, mp 112°–113°;

y) methyl 2,6-dimethyl-4-(1-phenyl-1H-pyrazol-3-yl)aminophenyl 1,5-pentanedioate, mp 108°–109°;

z) methyl 2,6-dimethyl-4-(1-phenyl-1H-pyrazol-3-yl)aminophenyl 1,4-butanedioate, mp 90°–91°;

aa) 3,6-dimethoxy-2-methyl-4-(1-phenyl-1H-pyrazol-3yl)aminophenyl acetate, mp 132°–134°;

ab) 2,6-dimethyl-4-[N-methyl-N-(1-phenyl-1H-pyrazol-3-yl)]aminophenyl ethanoate, mp 111°–112°;

ac) 2,3,5,6-tetramethyl-4-(1-phenyl-1H-pyrazol-3-yl)aminophenyl acetate, mp 179°–180°;

ad) 2,6-dichloro-4-(1-phenyl-1H-pyrazol-3-yl)aminophenyl acetate, mp 169°–170°;

ae) 2,6-dimethyl-4-(1-phenyl-1H-pyrazol-3-yl)aminophenyl phenylmethoxyacetate, mp 101°–101.5°;

af) 2,5-dimethoxy-4-(1-phenyl-1H-pyrazol-3-yl)aminophenyl acetate, mp 149°–150°;

ag) Benzene-1,4-dicarboxylic acid, mono-[2,6-dimethyl-4-(1-phenyl-1H-pyrazol-3-yl)aminophenyl]-ester, monophenylmethyl ester, mp 169°–171°.

Example 5

2,6-bis(1,1-dimethylethyl)-4-(N-methyl-N-[1-phenyl-1H-pyrazol-3-yl]amino)phenyl acetate To 2,6-bis (1,1-dimethylethyl)-4-(N-methyl-N-[1-phenyl-1H-pyrazol-3-yl]amino)phenol (0.6 g) in dry tetrahydrofuran (15 ml) at −78° under nitrogen was added butyl lithium (1.29 ml of 1.4M hexane solution). After 10 minutes acetyl chloride (0.2 ml) was added. The reaction was left for 16 hours, poured into water and extracted with ethyl acetate. Evaporation, and chromatography (silica, dichloromethane/hexane [1:1]) of the residue, followed by recrystallisation from hexane at −20° gave the title compound (0.35 g), mp 102°–103°.

Example 6

Using the appropriate acyl chlorides and phenols, the following compounds were prepared by the method of Example 5:

a) 2,6-bis(1,1-dimethylethyl)-4-(N-methyl-N-[1-phenyl-1H-pyrazol-3-yl]amino)phenyl methoxyacetate, mp 102°–103°;

b) 2,6-bis-(1,1-dimethylethyl)-4-(1-phenyl-1H-pyrazol-3-yl)aminophenyl acetate, mp 186°–187°; position of acetyl confirmed by NOE difference spectrum.

2,6-bis(1,1-dimethylethyl)-4-[(1-methyl-1H-pyrazol-3-yl)amino]-phenyl acetate 2,6-bis(1,1-dimethylethyl)-4-(2-oxazolylamino)-phenyl acetate 4-[(6-chloropyrazinyl)amino]-2,6-bis(1,1-dimethylethyl)-phenyl acetate 2,6-bis(1,1-dimethylethyl)-4-(1H-1,2,3-triazol-4-yl amino)-phenyl acetate 2,6-bis(1,1-dimethylethyl)-4-(4-pyrimidinylamino)-phenyl acetate 2,6-bis(1,1-dimethylethyl)-4-[(4-methyl-2-pyrimidinyl) amino]-phenyl acetate 2,6-bis(1,1-dimethylethyl)-4-(2-pyrimidinylamino)-phenyl acetate 4-[(3,6-dichloro-4-pyridazinyl)amino]-2,6-bis(1,1-dimethylethyl)-phenyl acetate 2,6-bis(1,1-dimethylethyl)-4-(4-pyridazinylamino)-phenyl acetate 6-[[3,5-bis(1,1-dimethylethyl)-4-acetoxyphenyl]amino]-3-pyridazinemethanol phenyl acetate 4-[(6-chloro-3-pyridazinyl)amino]-2,6-bis(1,1-dimethyl)-phenyl acetate 2,6-bis(1,1-dimethylethyl)-4-[(6-ethoxy-3-pyridazinyl) amino]-phenyl acetate 2,6-bis(1,1-dimethylethyl)-4-[(6-methyl-3-pyridazinyl) amino]-phenyl acetate 2,6-bis(1,1-dimethylethyl)-4-(3-pyridazinylamino)-phenyl acetate 2,6-(1,1-dimethylethyl)-6-(1-methylethyl)-4-(pyrazinyl amino)-phenyl acetate 2,6-bis(1,1-dimethylethyl)-4-(4H-1,2,4-triazol-4-ylamino)-phenyl acetate 2,6-bis(1,1-dimethylethyl)-4-(pyrazinylamino)-phenyl acetate 2,6-dimethyl-4-(pyrazinylamino)-phenyl acetate 2,6-bis(1,1-dimethylethyl)-4-(1H-imidazol-2-ylamino)-phenyl acetate 2,6-bis(1,1-dimethylethyl)-4-[(3-phenyl-1,2,4-thia diazol-5-yl)amino]-phenyl acetate 2,6-bis(1,1-dimethylethyl)-4-(1,2,4-triazin-3-ylamino)-phenyl acetate 2,6-bis(1,1-dimethylethyl)-4-[(2-methyl-3-thienyl) amino]-phenyl acetate 2,6-bis(1,1-dimethylethyl)-4-[(5-methyl-1,3,4-thia diazol-2-yl)amino]-phenyl acetate 2,6-bis(1,1-dimethylethyl)-4-[(1-methyl-1H-pyrazol-5-yl)amino]-phenyl acetate 2,6-bis(1,1-dimethylethyl)-4-(1H-pyrazol-3-ylamino)-phenyl acetate 2,6-bis(1,1-dimethylethyl)-4-(pyrazinylamino)-phenyl acetate 4-[(4-amino-5-pyrimidinyl)amino]-2,6-bis(1,1-dimethyl ethyl)-phenyl acetate 2,6-bis(1-methylethyl)-4-(pyrazinylamino)-phenyl acetate 2,6-bis(1,1-dimethylethyl)-4-[(6-methoxypyrazinyl) amino]-phenyl acetate Methyl 6-[[3,5-bis(1,1-dimethylethyl)-4-acetoxy phenyl]amino]-3-pyridazinecarboxylate 2,6-bis(1,1-dimethyl)-4-[(6-methoxy-3-pyridazinyl) amino]-phenyl acetate Methyl 5-[[3,5-bis,(1,1-dimethylethyl)-4-hydroxy phenyl]amino]-pyrazinecarboxylate 2,6-bis(1,1-dimethylethyl)-4-[(5-phenylpyrazinyl)amino]-phenyl acetate 2,6-bis(1,1-dimethylethyl)-4-[(5-methylpyrazinyl)amino]-phenyl acetate 2,6-bis(1,1-dimethylethyl)-4-(5-pyrimidinylamino)-phenyl acetate 2,6-bis(1,1-dimethylethyl)-4-(4-pyridazinylamino)-phenyl acetate 2-(1,1-dimethylethyl)-6-(1-methylethyl)-4-(3-pyridazinylamino)-phenyl acetate 2,3,6-trimethyl-4-(pyrazinylamino)-phenyl acetate 4-[(6-chloro-4-pyrimidinyl)amino]-2,6-bis(1,1-dimethyl ethyl)-phenyl acetate 5-[[3,5-bis(1,1-dimethylethyl)-4-acetoxyphenyl]amino]-pyrazinemethanol 2,3,6-trimethyl-4-(2-pyrimidinylamino)-phenyl acetate 2,6-bis(1,1-dimethylethyl)-4-[(4,6-dimethyl-2-pyrimidin yl)amino]-phenyl acetate 2-(1,1-dimethylethyl)-6-(1-methylethyl)-4-(1H-pyrazol-3-ylamino)-phenyl acetate 2,6-bis(1,1-dimethylethyl)-4-(1H-1,2,4-triazol-3-yl amino)-phenyl acetate 2,6-bis(1,1-dimethyl)-4-[(2-methyl-2H-1,2,3-triazol-4-yl)amino]-phenyl acetate 2,6-bis(1,1-dimethylethyl)-4-[(1-methyl-1H-1,2,3-triazol-4-yl)amino]-phenyl acetate 2,6-bis(1,1-dimethylethyl)-4-[(5-methyl-3-isoxazoly) amino]-phenyl acetate Methyl 2-thiophenecarboxylate 3-[[3,5-bis(1,1-dimethyl ethyl)-4-acetoxyphenyl]amino]-phenyl acetate 2-6-bis(1,1-dimethylethyl)-4-[(1-methyl-1H-pyrazol-4-yl)amino]-phenyl acetate 2,6-bis(1,1-dimethylethyl)-4-(1H-[pyrazol-4-ylamino)-phenyl acetate Ethyl 1H-pyrazol-4-carboxylate 5-[[3,5-bis(1,1-di methylethyl)-4-acetoxyphenyl]amino]-1-methyl 2,6-bis(1,1-dimethylethyl)-4-[(1,3-diphenyl-1H-pyrazol-5-yl)amino]-phenyl acetate 2,6-bis(1,1-dimethylethyl)-4-[(1-methyl-3-phenyl-1H-pyrazol-5-yl)amino]-phenyl acetate 2,6-bis(1,1-dimethylethyl)-4-[(1-propyl-1H-pyrazol-5-yl)amino]-phenyl acetate 2,6-bis(1,1-dimethylethyl)-4-[(1-propyl-1H-pyrazol-3-yl)amino]-phenyl acetate 2,3,6-trimethyl-4-(1H-pyrazol-3-ylamino)-phenyl acetate 2,6-bis(1,1-dimethylethyl)-4-[(6-methyl-3-pyridazinyl) amino]-phenyl acetate 2,6-bis(1,1-dimethylethyl)-4-(pyrazinylamino)-phenyl acetate N-oxide 2,6-bis(1,1-dimethylethyl)-4-[(2-methyl-3-thienyl-)amino]-phenyl acetate 2,6-bis(1,1-dimethylethyl-4-[(5,6-dimethyl-1,2,4-triazin-3-ylamino]-phenyl acetate 2,6-bis(1,1-dimethylethyl)-4-(1,3,4-thiadiazol-2-yl amino)-phenyl acetate 2,6-bis(methylethyl)-4-(1H-pyrazol-3-ylamino)-phenyl acetate

Example 7

1,4-Butanedioic acid, mono(2,6-dimethyl-4-[1-phenyl-1H-pyrazol-3-yl]aminophenyl) ester To 4-(1-phenyl-1H-pyrazol-3-yl)amino-2,6-dimethyl phenol (1.8 g) in dry dichloromethane (30 ml) and triethylamine (2.25 ml) at 0° under nitrogen was added succinic anhydride (0.84 g). The mixture was stirred at room temperature for 16 hours then poured into water. The organic phase was dried and evaporated. The resultant oil was chromatographed (silica, 2% methanol/dichloromethane) to give the title product (1.5 g), mp 160°–161° after crystallisation from hexane/ethyl acetate.

Example 8

The following compound was prepared by the method of Example 7:

a) 1,5-pentanedioic acid, mono(2,6-dimethyl-4-[1-phenyl-1H-pyrazol-3-yl]aminophenyl ester, mp 138°–140°;

Example 9

2,6-Dimethyl-4-(1-phenyl-1H-pyrazol-3-yl)aminophenyl 2-oxopropanoate 1,1'-carbonyldiimidazole (4.9 g) was added batchwise to pyruvic acid (2.6 g) in dichloromethane (100 ml), and after 0.5 hours 2,6-dimethyl-4-(1-phenyl-1H-pyrazol-3-yl) aminophenol (2.8 g) was added. The mixture was left for 16 hours, then evaporated, and the residue was chromatographed (silica, dichloromethane) to give, after crystallisation (hexane/ethyl acetate), the title product (1.0 g) mp 123°–125°.

Example 10

The following compounds were prepared by the method of Example 9:

a) 2,6-dimethyl-4-(1-phenyl-1H-pyrazol-3-yl)aminophenyl N-[(phenylmethoxy)carbonyl]glycinate, mp 142°–143°;

b) 2,6-dimethyl-4-(1-phenyl-1H-pyrazol-3-yl)aminophenyl 4-dimethylaminobutanoate, mp 83°–85°.

Example 11

2,6-Dimethyl-4-phenyl-1H-pyrazol-3-yl)aminophenyl acetate

The product from Example 1 was refluxed in toluene with 5% palladium on charcoal (0.15 g) for 4 hours. Filtration, evaporation and chromatography (silica, dichloromethane/ethyl acetate [95:5]) of the residue gave the title compound (0.07 g), mp 114°–116° (from cyclohexane); further polymorph, mp 134°.

Analysis found: C, 71.2; H, 6.1; N, 12.85% Calculated for $C_{19}H_{19}N_3O_2$: C, 70.9; H, 5.9; N, 12.5%.

Example 12

The following compound was prepared from the compound of Example 2a by the method of Example 11:

2,6-Dimethyl-4-(1-[3-trifluromethylphenyl]-1H-pyrazol-3-yl)aminophenyl acetate, mp 142°–143°.

Example 13

4-(1-Phenyl-1H-pyrazol-3-yl)amino-2,6-dipropylphenyl acetate 4-(1-Phenyl-1H-pyrazol-3-yl)amino-2,6-di(prop-2-enyl) phenyl acetate, from Example 3b), (3.5 g) in ethanol (150 ml) was hydrogenated at atmospheric pressure over 10% palladium on charcoal to afford, after crystallisation from cyclohexane, the title product (1.8 g), mp 71°–74°.

Example 14

Using the method of Example 13, the following compounds were obtained from the indicated precursors:

a) 2,6-Dimethyl-4-(1-phenyl-1H-pyrazol-3-yl)aminophenyl hydroxyacetate, mp 155°–157° b) 4-(1-Cyclohexyl-1H-pyrazol-3-yl)amino-2,6-dimethylphenyl hydroxyacetate, mp 160°–164° a) and b) were prepared from 2,6-dimethyl-4-(1-phenyl-1H-pyrazol-3-yl)aminophenyl phenylmethoxyacetate by hydrogenation at 5 atmospheres for 6 days and separation of the resulting mixture of compounds by chromatography (silica, dichloromethane/ethyl acetate (9:1)).

c) 2,6-Dimethyl-4-(1-phenyl-1H-pyrazol-3-yl)aminophenyl glycinate hydrochloride, prepared from Example 10a and followed by treatment with ethereal hydrogen chloride, mp 230°-231° d) Benzene-1,4-dicarboxylic acid, mono-[2,6-dimethyl-4-(1-phenyl-1H-pyrazol-3-yl)aminophenyl]ester, prepared from the monobenzyl ester, from the example 4ag) mp 221°-222°.

Example 15

2,6-Dimethyl-4-(1-phenyl-1H-pyrazol-3-yl)aminophenyl cyanoacetate 2,6-Dimethyl-4-(1-phenyl-1H-pyrazol-3-yl)aminophenyl chloroacetate, Example 4k, (1 g) and sodium cyanide (0.5 g) stirred in dimethyl sulfoxide for 16 hours gave, after dilution with brine, extraction with ethyl acetate and subsequent evaporation, the title compound (0.3 g), mp 116°-117° (from ethyl acetate/hexane).

Example 16

3-[2,6-Dimethyl,4-(1-phenyl-1H-pyrazol-3-yl)aminophenoxycarbonyl]-1]-1-methylpyridinium iodide 2,6-Dimethyl-4-(1-phenyl-1H-pyrazol-3-yl)aminophenyl 3-pyridinecarboxylate, Example 4o), (0.5 g) was refluxed in methyl iodide (100 ml) for 4 days, the unreacted methyl iodide removed by evaporation and the title product (0.15 g) obtained by trituration of the resulting oil with ether, mp 150° (dec).

Example 17—Compositions

| a) For topical delivery to the skin Cosolvent type gel for topical application: | |
|---|---|
| Active ingredient | 0.5% |
| Hydroxypropyl cellulose | 1.0% |
| Ethanol | 90.0% |
| Water | to 100.0% |
| b) Ophthalmic delivery | |
| Active ingredient (micronized) | 2.0% |
| Carbopol 934P | 1.0% |
| Sodium hydroxide | to pH7 |
| Benzalkonium chloride | 0.01% |
| NaCl | 0.9% |
| Water | to 100.0% |
| c) Enema for rectal delivery | |
| Active ingredient (micronized) | 3.0% |
| Glycerol | 2.5% |
| Methyl parabens | 0.15% |
| Propyl parabens | 0.15% |
| Water | to 100.0% |
| d) Subcutaneous oily injection | |
| Active ingredient | 3.0% |
| Miglyol 812 N | to 100.0% |
| e) Nasal suspension | |
| Active ingredient (micronized) | 1.0% |
| Polysorbate 80 | 0.5% |
| Benzalkonium chloride | 0.01% |
| Glycerol | 2.4% |
| Avicel | 2.0% |
| Water | to 100.0% |

We claim:

1. A compound having the formula,

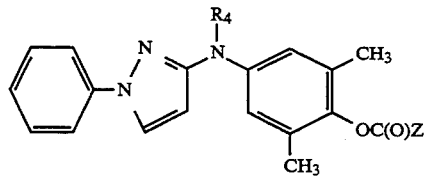

wherein,

Z represents pyridyl; phenyl optionally substituted by halogen; $C_{1-4}$ alkyl; or $C_{1-4}$ alkyl substituted by a substituent selected from methoxy, ethoxy, $C_{1-4}$ acyloxy, phenylmethoxy, or cyano;

$R_4$ represents H or $C_{1-3}$ alkyl;

or a pharmaceutically acceptable N-oxide, N-alkyl, salt, ester, or amide derivative thereof.

2. A compound in accordance with claim 1, selected from the group consisting of 2,6-dimethyl-4-(1-phenyl-1H-pyrazol-3-yl)aminophenyl butanoate, 2,6-dimethyl-4-(1-phenyl-1H-pyrazol-3-yl)aminophenyl 2,2-dimethylpropanoate, 2,6-dimethyl-4-(1-phenyl-1H-pyrazol-3-yl)aminophenyl benzoate, 2,6-dimethyl-4-(1-phenyl-1H-pyrazol-3-yl)aminophenyl 2-methylpropanoate, 2,6-dimethyl-4-(1-phenyl-1H-pyrazol-3-yl)aminophenyl methoxyacetate, 2,6-dimethyl-4-(1-phenyl-1H-pyrazol-3-yl)aminophenyl 3-pyridinecarboxylate, 2,6-dimethyl-4-(1-phenyl-1H-pyrazol-3-yl)aminophenyl 4-chlorobenzoate, 2,6-dimethyl-4-(1-phenyl-1H-pyrazol-3-yl)aminophenyl 3-methoxypropanoate, 2,6-dimethyl-4-(1-phenyl-1H-pyrazol-3-yl)aminophenyl acetoxyethanoate, methyl 2,6-dimethyl-4-(1-phenyl-1H-pyrazol-3-yl)aminophenyl propanedioate, methyl 2,6-dimethyl-4-(1-phenyl-1H-pyrazol-3-yl)aminophenyl 1,5-pentanedioate, methyl 2,6-dimethyl-4-(1-phenyl-1H-pyrazol-3-yl)aminophenyl 1,4-butanedioate, 2,6-dimethyl-4-[N-methyl-N-(1-phenyl-1H-pyrazol-3-yl)]aminophenyl ethanoate, 2,6-dimethyl-4-(1-phenyl-1H-pyrazol-3-yl)aminophenyl phenylmethoxyacetate, 2,6-dimethyl-4-(1-phenyl-1H-pyrazol-3-yl)aminophenyl cyanoacetate, and pharmaceutically acceptable N-oxide, N-alkyl, salt, ester, or amide derivatives thereof.

3. A compound having the formula,

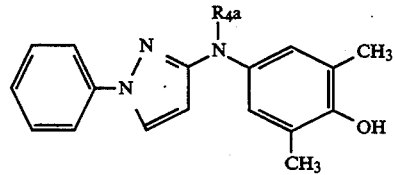

wherein $R_{4a}$ represents H or $C_{1-3}$ alkyl.

4. A compound in accordance with claim 1 which is 2,6-dimethyl-4-(1-phenyl-1H-pyrazol-3-yl)aminophenyl acetate, or a pharmaceutically acceptable salt thereof.

* * * * *